(12) United States Patent
McGregor et al.

(10) Patent No.: US 8,821,417 B2
(45) Date of Patent: Sep. 2, 2014

(54) METHOD OF MONITORING HUMAN BODY MOVEMENT

(71) Applicants: Stephen J. McGregor, Saline, MI (US); Erik Bollt, Potsdam, NY (US); Frank J. Fedel, Royal Oak, MI (US)

(72) Inventors: Stephen J. McGregor, Saline, MI (US); Erik Bollt, Potsdam, NY (US); Frank J. Fedel, Royal Oak, MI (US)

( * ) Notice: Subject to any disclaimer, the term of this patent is extended or adjusted under 35 U.S.C. 154(b) by 0 days.

(21) Appl. No.: 13/725,037

(22) Filed: Dec. 21, 2012

(65) Prior Publication Data

US 2013/0110011 A1 May 2, 2013

Related U.S. Application Data

(63) Continuation of application No. PCT/US2011/041456, filed on Jun. 22, 2011.

(60) Provisional application No. 61/357,196, filed on Jun. 22, 2010.

(51) Int. Cl.
*A61B 5/103* (2006.01)
*A61B 5/117* (2006.01)

(52) U.S. Cl.
USPC ............................. 600/587; 600/595

(58) Field of Classification Search
CPC ......................................................... A61B 5/00
USPC .................................................. 600/587, 595
See application file for complete search history.

(56) References Cited

U.S. PATENT DOCUMENTS

| | | | | |
|---|---|---|---|---|
| 4,375,674 A | * | 3/1983 | Thornton | 702/41 |
| 5,524,637 A | * | 6/1996 | Erickson | 600/592 |
| 5,562,104 A | * | 10/1996 | Hochberg et al. | 600/595 |
| 5,592,401 A | * | 1/1997 | Kramer | 702/153 |
| 5,615,132 A | * | 3/1997 | Horton et al. | 703/7 |
| 6,057,859 A | * | 5/2000 | Handelman et al. | 345/474 |
| 6,314,339 B1 | * | 11/2001 | Rastegar et al. | 700/260 |
| 7,148,878 B2 | * | 12/2006 | Hong et al. | 345/157 |
| 7,210,240 B2 | * | 5/2007 | Townsend et al. | 33/512 |
| 7,395,181 B2 | * | 7/2008 | Foxlin | 702/155 |
| 7,602,301 B1 | | 10/2009 | Stirling et al. | |
| 7,603,255 B2 | | 10/2009 | Case, Jr. et al. | |
| 7,634,379 B2 | | 12/2009 | Noble | |
| 7,637,959 B2 | | 12/2009 | Clausen et al. | |
| 7,670,303 B2 | | 3/2010 | Sato et al. | |
| 7,821,407 B2 | * | 10/2010 | Shears et al. | 340/573.1 |
| 7,988,647 B2 | * | 8/2011 | Bunn et al. | 600/595 |
| 8,118,712 B2 | * | 2/2012 | Thieberger et al. | 482/8 |
| 8,206,325 B1 | * | 6/2012 | Najafi et al. | 600/595 |

(Continued)

OTHER PUBLICATIONS

Armstrong et al., "Reliability of mechanomyography and triaxial accelerometry in the assessment of balance", Journal of Electromyography and Kinesiology, 2010, vol. 20, Issue 4, pp. 726-731.

(Continued)

*Primary Examiner* — Max Hindenburg
*Assistant Examiner* — May Abouelela
(74) *Attorney, Agent, or Firm* — MacMillan, Sobanski & Todd, LLC

(57) ABSTRACT

A method of monitoring human body movement includes measuring the motion of movable body parts using one or more measurement devices applied to the movable body parts during activity of the human body. A movement economy profile of the human body movement is calculated using the data from the measurement devices, where the movement economy includes determining movement relative to speed of the human body.

20 Claims, 2 Drawing Sheets

(56) References Cited

U.S. PATENT DOCUMENTS

| | | | |
|---|---|---|---|
| 8,323,190 B2* | 12/2012 | Vitiello et al. | 600/301 |
| 8,366,641 B2* | 2/2013 | Wang et al. | 600/595 |
| 8,405,510 B2* | 3/2013 | Shieh et al. | 340/573.1 |
| 8,608,671 B2* | 12/2013 | Kinoshita et al. | 600/595 |
| 2001/0031934 A1* | 10/2001 | Sarvazyan et al. | 600/587 |
| 2002/0143277 A1* | 10/2002 | Wood et al. | 600/595 |
| 2003/0139692 A1* | 7/2003 | Barrey et al. | 600/595 |
| 2004/0019382 A1 | 1/2004 | Amirouche et al. | |
| 2004/0116836 A1* | 6/2004 | Kawai et al. | 600/595 |
| 2005/0033200 A1* | 2/2005 | Soehren et al. | 600/595 |
| 2006/0000420 A1* | 1/2006 | Martin Davies | 119/174 |
| 2006/0058699 A1* | 3/2006 | Vitiello et al. | 600/546 |
| 2006/0079800 A1* | 4/2006 | Martikka et al. | 600/546 |
| 2006/0241521 A1* | 10/2006 | Cohen | 600/595 |
| 2006/0270943 A1* | 11/2006 | Kamataki et al. | 600/554 |
| 2007/0197938 A1* | 8/2007 | Tyson et al. | 600/587 |
| 2007/0219059 A1* | 9/2007 | Schwartz et al. | 482/8 |
| 2007/0270214 A1* | 11/2007 | Bentley | 463/30 |
| 2007/0276282 A1* | 11/2007 | Fukumura et al. | 600/546 |
| 2008/0009771 A1* | 1/2008 | Perry et al. | 600/587 |
| 2008/0285805 A1* | 11/2008 | Luinge et al. | 382/107 |
| 2009/0048070 A1* | 2/2009 | Vincent et al. | 482/8 |
| 2009/0048540 A1* | 2/2009 | Otto et al. | 600/595 |
| 2009/0069722 A1* | 3/2009 | Flaction et al. | 600/587 |
| 2009/0069724 A1* | 3/2009 | Otto et al. | 600/595 |
| 2009/0204031 A1* | 8/2009 | McNames et al. | 600/595 |
| 2009/0264789 A1* | 10/2009 | Molnar et al. | 600/544 |
| 2010/0010380 A1* | 1/2010 | Panken et al. | 600/587 |
| 2010/0010382 A1* | 1/2010 | Panken | 600/587 |
| 2010/0010383 A1* | 1/2010 | Skelton et al. | 600/587 |
| 2010/0010583 A1* | 1/2010 | Panken et al. | 607/62 |
| 2010/0063508 A1* | 3/2010 | Borja et al. | 606/88 |
| 2010/0094188 A1* | 4/2010 | Goffer et al. | 602/23 |
| 2010/0099539 A1* | 4/2010 | Haataja | 482/8 |
| 2010/0144414 A1* | 6/2010 | Edis et al. | 463/8 |
| 2010/0210975 A1* | 8/2010 | Anthony et al. | 600/595 |
| 2010/0228154 A1* | 9/2010 | Leuthardt et al. | 600/587 |
| 2010/0249672 A1* | 9/2010 | Ewing | 601/5 |
| 2010/0280335 A1* | 11/2010 | Carlson et al. | 600/301 |
| 2010/0280578 A1* | 11/2010 | Skelton et al. | 607/62 |
| 2011/0054359 A1* | 3/2011 | Sazonov et al. | 600/595 |
| 2011/0092337 A1* | 4/2011 | Srinivasan et al. | 482/8 |
| 2011/0118621 A1* | 5/2011 | Chu | 600/546 |
| 2011/0172562 A1* | 7/2011 | Sahasrabudhe et al. | 600/587 |
| 2011/0172564 A1* | 7/2011 | Drew | 600/587 |
| 2011/0208093 A1* | 8/2011 | Gross et al. | 600/587 |
| 2011/0218458 A1* | 9/2011 | Valin et al. | 600/595 |
| 2011/0270132 A1* | 11/2011 | Mezghani et al. | 600/587 |
| 2011/0275957 A1* | 11/2011 | Bhandari | 600/595 |
| 2012/0022406 A1* | 1/2012 | Hladio et al. | 600/587 |
| 2012/0029345 A1* | 2/2012 | Mahfouz et al. | 600/427 |
| 2012/0083714 A1* | 4/2012 | Yuen et al. | 600/587 |
| 2012/0092169 A1* | 4/2012 | Kaiser et al. | 340/573.1 |
| 2012/0139731 A1* | 6/2012 | Razoumov et al. | 340/573.1 |
| 2012/0197160 A1* | 8/2012 | Reinhardt et al. | 600/587 |
| 2013/0110011 A1* | 5/2013 | McGregor et al. | 600/595 |
| 2013/0274635 A1* | 10/2013 | Coza et al. | 600/595 |
| 2013/0324888 A1* | 12/2013 | Solinsky | 600/595 |

OTHER PUBLICATIONS

Bollt et al., "Control Entropy: A Complexity Measure for Nonstationary Signals", Mathematical Biosciences and Engineering, 2009, vol. 6, No. 1, pp. 1-25.

Fuller et al., "Posture-movement changes following repetitive motion-induced shoulder muscle fatigue", Journal of Electromyography Kinesiology, Dec. 2009, vol. 19, No. 6, pp. 1043-1052.

International Search Report and Written Opinion, PCT/US2011/041456, dated Nov. 17, 2011.

McGregor et al., "Control entropy identifies differential changes in complexity of walking and running gait patterns with increasing speed in highly trained runners", CHAOS, 2009, vol. 19, Issue 2, pp. 1-13.

McGregor et al., "Control Entropy of Gait: Does Running Fitness Affect Complexity of Walking?", Clinical Kinesiology, 2011, vol. 65, No. 1, pp. 9-17.

McGregor et al., "Control Entropy: What is it and What does it tell us?", Clinical Kinesiology, 2012, vol. 66, No. 1, pp. 7-17.

McGregor et al., "High Resolution MEMS Accelerometers to Estimate VO2 and Compare Running Mechanics between Highly Trained Inter-Collegiate and Untrained Runners", PLoS One, 2009, vol. 4, Issue 10, pp. 1-10.

McGregor et al., "Lower extremity fatigue increases complexity of postural control during a single-legged stance", Journal of NeuroEngineering and Rehabilitation, 2011, vol. 8, No. 43, pp. 1-10.

McGregor et al., "Performance Modeling in an Olympic 1500-M Finalist: A Practical Approach", Journal of Strength and Conditioning Research, 2009, vol. 23, Issue 9, pp. 2515-2523.

Parshad et al., "A Statistical Approach to the Use of Control Entropy Identifies Differences in Constraints of Gait in Highly Trained Versus UnTrained Runners", Mathematical Biosciences and Engineering, 2012, vol. 9, No. 1, pp. 125-148.

"Precision ±1.7 g, ±5 g, ±18 g Single-/Dual-Axis iMEMS® Accelerometer", Data Sheet ADXL103/ADXL203, Analog Devices, 2011, pp. 1-16.

Smith, "Notes from the Medical Director: Limb Loss in Children: Prosthetic Issues", InMotion Easy Read, 2006, vol. 16, Issue 3, pp. 1-8.

* cited by examiner

METHOD OF MONITORING HUMAN BODY MOVEMENT

RELATED APPLICATIONS

This application claims priority from U.S. Provisional Patent Application Ser. No. 61/357,196 filed Jun. 22, 2010, and entitled HIGH RESOLUTION MEMS ACCELEROMETERS TO ESTIMATE VO2 AND EVALUATE RUNNING MECHANICS, and PCT Application US2011/041456 filed Jun. 22, 2011. The entire contents of Application Ser. No. 61/357,196 and PCT Application US2011/041456 are hereby incorporated in their entirety.

TECHNICAL FIELD

This invention relates to monitoring human body movement, particularly in connection with fitness level assessment, exercise technique enhancement, and adaptation of prosthetic and orthotic devices to a human body.

BACKGROUND OF THE INVENTION

There has been increasing interest in recent years in the use of technology to assess training load in exercise and competitive runners in the field. Efforts have been made to utilize global positioning system (GPS) devices to record running speed and estimate running performance, but these devices exhibit relatively low resolution. A possible candidate that might serve as a means to assess training load for running is the accelerometer. The use of low resolution accelerometers to measure human movement is known. From a physiological perspective, they have commonly been used as mere activity monitors for the coarse-grained measurement of gross movements. In many cases, the goal of using these low resolution accelerometers has been in an attempt to objectively determine energy expenditure during unstructured activities of daily living.

It is known to investigate the relationship between activity monitor accelerometers and VO2 in trained runners in an attempt to objectively quantify external work of a dynamic activity such as running. Further, accelerometers have been used in the field of biomechanics for the purposes of gait analysis. It would be advantageous if there could be developed a method to objectively quantify external work or mechanics of a dynamic activity such as running. Such a method could enhance knowledge of training techniques for exercise activities and racing, and would be applicable to a number of forms of exercise, including running, walking and swimming. Further, it would be advantageous if there could be developed a method analyzing the quality or economy of exercise and other physical activity.

SUMMARY OF THE INVENTION

According to this invention there is provided a method of monitoring human body movement. The method includes measuring the motion of movable body parts using one or more measurement devices applied to the movable body parts during activity of the human body. A movement economy profile of the human body movement is calculated using the data from the measurement devices, where the movement economy includes determining movement relative to speed of the human body.

According to this invention there is also provided a method of monitoring human body activity including measuring the motion of movable body parts using one or more measurement devices applied to the movable body parts during activity of the human body, where the measurement devices are arranged to measure acceleration in three axes. The ratio of the measured movement along of one of the axes to the resultant movement along all three of the axes is calculated.

According to this invention there is also provided a method of monitoring human body activity wherein the method includes measuring the motion of movable body parts using one or more measurement devices applied to the movable body parts during activity of the human body. The control entropy of the movement of the human body is calculated. The control entropy is compared with a database containing control entropy information of other exercise subjects.

According to this invention there is also provided a method of monitoring human body including measuring the motion of a movable prosthetic or human body part having an associated orthotic using one or more measurement devices applied to the movable prosthetic or human body part having an associated orthotic during activity of the human body. A movement economy profile of the human body movement is calculated using the data from the measurement devices, where the movement economy includes determining movement relative to speed of the human body. The prosthetic or orthotic is modified in response to the movement economy profile information.

According to this invention there is also provided a method of monitoring human body activity including measuring the motion of a movable prosthetic or human body part having an associated orthotic using one or more measurement devices applied to the movable prosthetic or human body part having an associated orthotic during activity of the human body. The control entropy of the movement of the prosthetic or human body part having an associated orthotic is calculated and the prosthetic or orthotic is modified in response to the control entropy.

According to this invention there is also provided a method of monitoring human body activity. The method includes measuring the motion of movable body parts using one or more measurement devices applied to the movable body parts during activity of the human body, where the motion occurs over a period of time and the measurement is made at multiple times during the period of time. The control entropy of the movement of the human body over the period of time is calculated. A determination is made as to when a state of fatigue for the human body is reached based on the calculated control entropy.

According to this invention there is also provided a method of monitoring human body activity including measuring the motion of movable body parts, including a foot of the human body, using one or more measurement devices applied to the movable body parts during activity of the human body. The body parts include one or more of a shoe and a heel. A movement profile of the human body movement is developed using the data from the measurement devices.

Various advantages of this invention will become apparent to those skilled in the art from the following detailed description of the preferred embodiment, when read in light of the accompanying drawings.

DETAILED DESCRIPTION OF THE INVENTION

Figure 1:
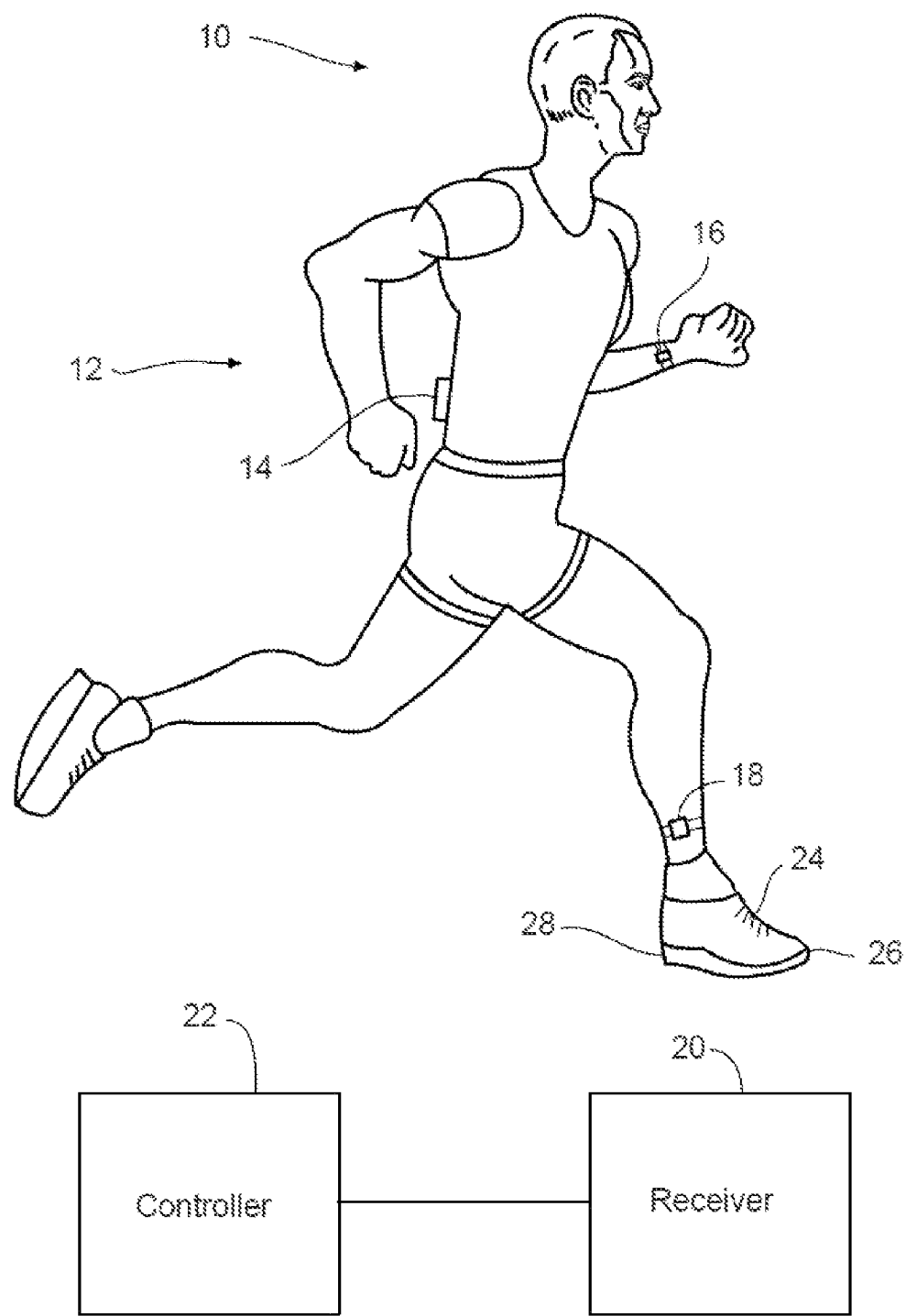
FIG. 1 is a schematic view of a running human subject.

The techniques introduced here include methods for using wearable high resolution accelerometers (HRA) and other optionally included sensors as components of an Extended Body Sensing Network (EBSN). The techniques further include the application of linear and non-linear algorithms including entropy analysis to the data obtained by the EBSN for evaluation and modification of human movement. For example, these techniques can be used for the determination and characterization of running mechanics, to quantify workload and model performance in running, and to determine appropriate adjustment of orthoses and prostheses in clinical practice. The techniques further include methods for using Control Entropy (CE) of HRA for the determination of appropriate adjustment of orthotics and prosthetics in clinical practice and for the determination of constraints of movements, including running.

Components of an EBSN can be used for measuring human movement mechanics including work output, efficiency, economy, mechanical loading and many other parameters in a non-constrained environment. For example, kinematic and kinetic parameters including scalar and vector measurements such as linear and angular displacement, velocity (first derivative of displacement), acceleration (second derivative of displacement), and jerk (third derivative of displacement), and force, power, work, moment of inertia, etc., can be measured using an EBSN. Similarly, physiologic measures such as, heart rate, blood pressure, O2 saturation, galvanic skin response, skin temperature, core temperature, EMG, iEMG, EEG, plethysmography and others can be measured using an EBSN.

Using HRA affixed to the approximate center of mass (COM), to measure is accelerations along the vertical, medial/lateral and anterior-posterior axes can identify differences in running mechanics between trained and untrained runners. The same approach can identify differences in running mechanics between highly trained runners, and equally fit, but lesser trained runners or runners (or other athletes) of lesser ability. These differences can explain in large part differences in running economy (O2 cost) between these two groups. Therefore, an HRA sensor mounted on the lower back of the subject, superficial to the L3 vertebra, can be used to examine and diagnose running mechanics in runners and other exercisers, and provide insight into ways running economy may be improved.

Further, additional EBSN sensor nodes applied to other parts of the body have provided data that support the concept that arm movement in trained runners can explain some of the oxygen cost of running that cannot be explained by speed or COM HRA alone. Additional EBSN sensors applied to the shank (shin) can determine factors such as the work to swing the shank, as well as impact dissipation between the shank and COM. This information could prove useful in predicting soft tissue injury from overuse or loading.

All of this can be extended to activities which are not quite as two dimensional as running. COM movement during running occurs mostly along two planes—anterior-posterior and to a lesser degree, vertically but with minimal medial/lateral excursion). The results demonstrate a strong relationship between total work done as measured using the EBSN components and physiologic cost. Further, while physiologic cost is of critical importance, mechanical impact is also an issue in many situations (e.g., for an individual with a compromised musculoskeletal system who cannot dissipate externally-imposed forces effectively, such as an amputee wearing an artificial limb, or someone wearing an orthosis).

Finally, using onboard algorithms to determine speed or external measures such as GPS, the economy of movement relative to speed as described below can be performed in the field, and not limited to stationary situations such as exercise machines and laboratory environments.

The use of Extended Body Sensing Network (EBSN) to model performance in running can be used to determine the impact incurred, and/or the physical work performed (physiological cost of the work performed) more precisely than running speed alone. A sensor network utilizing COM-EBSN as well as arm and possibly shank mounted EBSN sensors can be used to quantify the work of running under very dynamic conditions (e.g. rapidly changing speed), and also under conditions where GPS is inaccurate (on outdoor tracks) or not functional (indoors).

The Extended Body Sensing Network (EBSN) can also be used for the determination appropriate adjustment of orthotics and prosthetics in clinical practice. EBSN can be used to determine mechanics of walking, running or other movements in individuals with orthotic or prosthetic appliances. Not only can the network be used to determine mechanics of locomotion, but it can be used to quantify changes in mechanics of movement with adjustment of the appliances in order to optimize function. When an external appliance (e.g. prosthesis or orthosis) is applied to an individual, alteration of body mechanics occurs. This could apply to other external appliances besides prostheses or orthoses. Kinetic changes are required since internal work is compromised. In the case of prosthetic appliances, since muscles are absent in a prosthesis, they are not producing force as they are in an unaffected limb. Also, kinematic changes naturally result since the moment of inertia is typically affected. The weight and location of COM of the prosthetic appliance differs from the contra-lateral/unaffected limb. Quantification of the differences in kinematics between the affected and unaffected limb for a given prosthetic or orthotic appliance on an individual can be measured using EBSN and a database of resulting changes can be developed.

As shown in FIG. 1, the subject human body engaged in an exercise activity is indicated at 10. It can be seen that the human body is moving through space laterally or horizontally relative to the running surface, or in the case of an exercise machine, relative to a component of the exercise machine, such as the running surface of a treadmill. The subject has an Extended Body Sensing Network 12 that includes a high resolution accelerometer 14 fixed to the lower back of the subject, approximately at the L3 vertebra. Other locations to simulate the center of mass of the subject exerciser can also be used. In one embodiment the HRA 14 was placed anatomically at the intersection of the sagittal and axial planes on the posterior side of the body in line with the top of the iliac crest in order to approximate the center of mass.

Additional high resolution accelerometers 16 and 18 are fixed to the subject's lower arm and leg, respectively. Any suitable accelerometer can be used, but the best results will require a high resolution accelerometer. Advantageously, the high resolution accelerometer is a wireless device although wired devices can also be used. The high resolution accelerometer can have a signal frequency of at least two hundred Hz or more. An example of a high resolution accelerometer that can be used is a model ADXL210 (G-link Wireless Accelerometer Node±10 g Microstrain, Inc., Williston, Vt.), providing signals at a rate of 1000 Hz. This provides essentially a continuous monitoring or streaming of the data from the accelerometers to a data gathering device, such as a receiver 20 associated with a controller 22. The controller can be any processor, such as a CPU or computer, capable of being programmed and providing such functions as control and data storage for the operation of the exercise analysis system. The accelerometers provide a measure of the movement of the human body during the activity and transmit the data to the receiver. Alternately, the data can be stored in the accelerometer device itself for later downloading to the controller 22.

In one embodiment, as shown in FIG. 1, the accelerometers are arranged to measure acceleration in along three axes, i.e., in the vertical, medial/lateral and anterior/posterior planes. Although the use of high resolution accelerometers is described above, there are a number of other measurement devices that can be applied to the movable body parts during activity of the human body for the collection of data. For example, gyroscopes and GPS devices can also be used as the measurement devices, either alone or in combination with other measurement devices.

The data from these three accelerometers can be manipulated to form useful information regarding the exercise activity. It is to be understood that any number of accelerometers can be applied to movable body parts and used to collect data during the exercise activity. An algorithm in the controller can be used to determine the movement economy profile of the human body movement. An example of an algorithm that can be used is as follows:

$$X_{EC} = X\text{rms}/\text{speed}$$

The calculation can be made for each axis (VT, ML, AP and RES), where X is the respective axis, e.g. vertical VT, medial/lateral ML, anterior/posterior AP, or resultant RES (sum of VT, ML and AP), and speed is the speed of the stage being calculated, i.e., the speed of the subject human body undergoing the exercise activity. The term "RES" is the resultant of the three axes. Where the three axes are the VT, ML and AP axes, the resultant is determined as follows:

$$\text{RES}_{RMS} = \sqrt{VT_{RMS}^2 + ML_{RMS}^2 + AP_{RMS}^2}$$

The term "RMS" refers to the root mean square. In the general case, the movement economy profile can be determined using the following equation:

$$x_{rms} = \sqrt{(x_1^2 + x_2^2 + x_3^3 + \ldots + x_N^2)/N}$$

These calculations lead to economy valuations of acceleration relative to speed for each axis in the vertical ($VT_{Ec}$), medial/lateral ($ML_{Ec}$), anterior posterior ($AP_{Ec}$) and resultant ($RES_{Ec}$) in g/km/h. Thus, a movement economy profile of the human body movement can be calculated using the data from the measurement devices, where the movement economy includes determining movement relative to speed of the human body. It is to be understood that the movement economy can be calculated using other methods, such as, for example, using peak values or peak to peak values of the signal instead of rms values.

In one embodiment, the movement economy profile information is compared with a database containing data pertaining to movement economy profile information of other subjects. Economy profile data can be collected from a number of subjects, and a comparison of the data from a particular subject to the population of data in the database will provide valuable insight as to the relative economy of the exercise activity of the particular subject exerciser. This will provide information regarding movement in one or more planes that is excessive compared to that of more economical runners contained in the database. From this an individual or coach could identify particular movement patterns that are excessive and can be reduced through training or practice.

Once the economy profile is determined, the exerciser can then modify the exercise activity in response. For example, if the comparison to the database indicates excessive medial/lateral movement of the arms, the exerciser can modify the running style to reduce the movement of the arms along the medial/lateral axis. One useful aspect of the comparison process is that comparison with highly trained runners (or other exercisers) can result in the identification of areas where the subject exerciser deviates significantly from the highly trained runners or good runners.

Once the movement economy profile information is developed, the information can handled in a number of ways. The movement economy profile information can be transmitted to a web-based device, stored in a data storage device, sent to a display, compared with a database containing data pertaining to movement economy profile information of other subjects, and printed. User data can be forwarded to a remote server via a user communication device. A virtual coach application can be provided in the remote server, with the application comparing the reference training data with the user data and providing a corrective feedback to the end-user (exerciser, trainer or coach). The corrective feedback to the end-user may be provided on the user communication device such as a personal computer, digital assistant, or mobile phone.

In one embodiment the gathering of the data from the accelerometers during movement of the human body occurs when the human body is moving in space and not on a stationary exercise machine. For example, data can be collected by a runner on an outdoor roadway or trail, and exercise data gathering is not limited to subjects on stationary exercise machines.

One of the aspects of the method of monitoring human activity is that the corrections or modifications of the human activity can be undertaken while the human body is participating in the exercise activity. For example, once the economy profile or control entropy is calculated based on the data from the extended body sensing network, the modifications can be made with real time feedback. This can be used to provide the exerciser with contemporaneous feedback. In one embodiment, a monitoring device, not shown, containing an alarm providing audible or visual signals, is worn by the exerciser, with the alarm sounding whenever the exercise economy or control entropy exceeds an established upper or lower boundary.

The data collected by the accelerometers or other movable body parts using one or more of the measurement devices can be processed for further valuable information. An algorithm in the controller can be used to determine the ratio of the of the measured movement along of any one of several axes to the resultant movement along all three of the axes. For example, where the measurement devices are arranged to measure acceleration in three axes, the ratio of the measured movement along of one of the axes to the resultant movement along all three of the axes can be calculated. To determine the contribution of accelerations specific to each axis as a proportion of resultant (RES) accelerations, values can be calculated by the equation $$X_{Ra} = X_{rms}/\text{RES}_{rms}$$

where X is the respective axis (e.g. VT, ML, and AP). This calculation results in a unitless ratio for each axis, $VT_{Ra}$, $ML_{Ra}$ and $AP_{Ra}$. Although in this example, the three axes represent the vertical, medial/lateral, and anterior/posterior axes, the axes can be aligned in any suitable manner with respect to the human body, and any number of axes can be used. As shown in the drawing, the measurement devices 14, 16, and 18 are arranged on the approximate center of mass COM of the body, on one or more arms of the body, and on one or more legs of the body, respectively.

The movement ratio information determined using this technique can be compared with a database containing data pertaining to movement ratio information of other subjects.

Once a comparison is made, the movement of the subject's body can be modified in response. For example, if the accelerometer information measured along the medial/lateral axis is proportionally higher than expected when compared with the database, a response might be to modify the running form to reduce the movement along that axis.

Control entropy (CE) is a measure of the irregularity of the movement of the moving body parts of the subject exerciser. If the movement is regular, the control entropy is low, and if irregular or complex, the control entropy is higher. The control entropy based on data from the Extended Body Sensing Network can be used for the determination of appropriate adjustment of orthotics and prosthetics in clinical practice. A non-linear algorithm for control entropy can be applied to signals obtained from EBSN sensors including HRAs, as explained below, for use with individuals fitted with orthotic or prosthetic appliances. Control system constraints can be inferred from the entropy of the signal obtained from HRA sensors. For example, a runner physically constrained by a painful knee joint will exhibit a higher control entropy.

In a specific example, the CE algorithm can be applied to axial signals obtained from a triaxial HRA mounted superficial to the L3 vertebra to approximate the COM. The constraints imposed on the individual subject by the appliance will be quantified, and optimization of appliance fitting for the prosthesis or orthoses can be obtained through monitoring the CE analysis of the HRA in response to adjustments. Further, CE can be applied to signals obtained from other network sensors, such as those on an unaffected limb, or from sensors mounted on, or associated with the orthotic or prosthetic device in order to determine the varying constraints in the integrated system, and to obtain minimal total system constraints.

To define control entropy via correlation sums: Let $\{z_i\}_{i=1}^N$ be a scalar time series where data is taken on a uniform time grid. Without loss of generality, unit spacing in time is assumed. For embedding dimension of m, let $v_i=(z_i, z_{i-1}, \ldots, z_{i-m+1})$ be a delay embedding, where it is assumed a unit embedding delay. The correlation sum is given by $$C_2(\{z_i\}; m, r, T) = \frac{1}{N_{pairs}} \sum_{i=m}^{N} \sum_{j<i-T} \Theta(r - \|v_i - v_j\|_\infty),$$

where $\Theta$ is the heaviside function, r is a parameter defining a neighborhood, and $N_{pairs}=(N-m+1)(N-m-w+1)/2$ is the total number of pairs of delay vectors. Integer parameter $T \geq 1$ is the Theiler window, which mitigates the effects of time correlation in the data. Next, $$\hat{h}_2(\{z_i\}; m, r, T) = \ln\left(\frac{C_2(\{z_i\}, m, r, T)}{C_2(\{z_i\}, m+1, r, T)}\right).$$

Control entropy is essentially equivalent to SampEn, which motivates the choice of symbology for the windowed version. Consider time series $\{z_i\}_{i=1}^n$: Define $$SE(j+J, w, \{z_i\}_{i=1}^n; m, r, T) := \hat{h}_2(\{z_i\}_{i=1+j}^{w+j}; m, r, T),$$
$$0 \leq j \leq n-w,$$

where J represents a time offset. SE assigns an entropy value to a time window of the dataset. J allows association of that entropy with a specific instant in time. Choosing J=w associates the entropy of the window with the ending time of that window, while J=w/2 would associate that entropy with the time at the middle of the window. Control entropy is defined by applying SE to the first difference, $$CE(j+J, w, \{x_i\}_{i=0}^n; m, r, T) := SE(j+J, w, \{x_i - x_{i-1}\}_{i=1}^n; m, r, T), \quad 0 \leq j \leq n-w-1.$$

The CE algorithm signal obtained from HRA can be applied to determine constraints experienced by a subject during running. The constraints can be compared to an optimal constraint model and then used to improve the running or walking mechanics of the subject. In addition, the control entropy calculated from the data gathered by the sensors in the network, such as those attached to the arm, wrist, shank or other parts of the body, can be compared with a database containing control entropy information of other exercise subjects. In response to this comparison, adjustments to the exercise activity, gait or form can be made, including modifying the movement of the human body in response to the control entropy information. In another aspect, the control entropy information can be used to determine when an exercise subject reaches a state of exhaustion. As an exercise subject progresses through an exercise program, the control entropy will typically become lower over time. Variation in the movement is minimized as the subject tires. At some point the control entropy diminishes to a pre-set level, and it can be said that the subject has reached a state of exhaustion.

Figure 2:
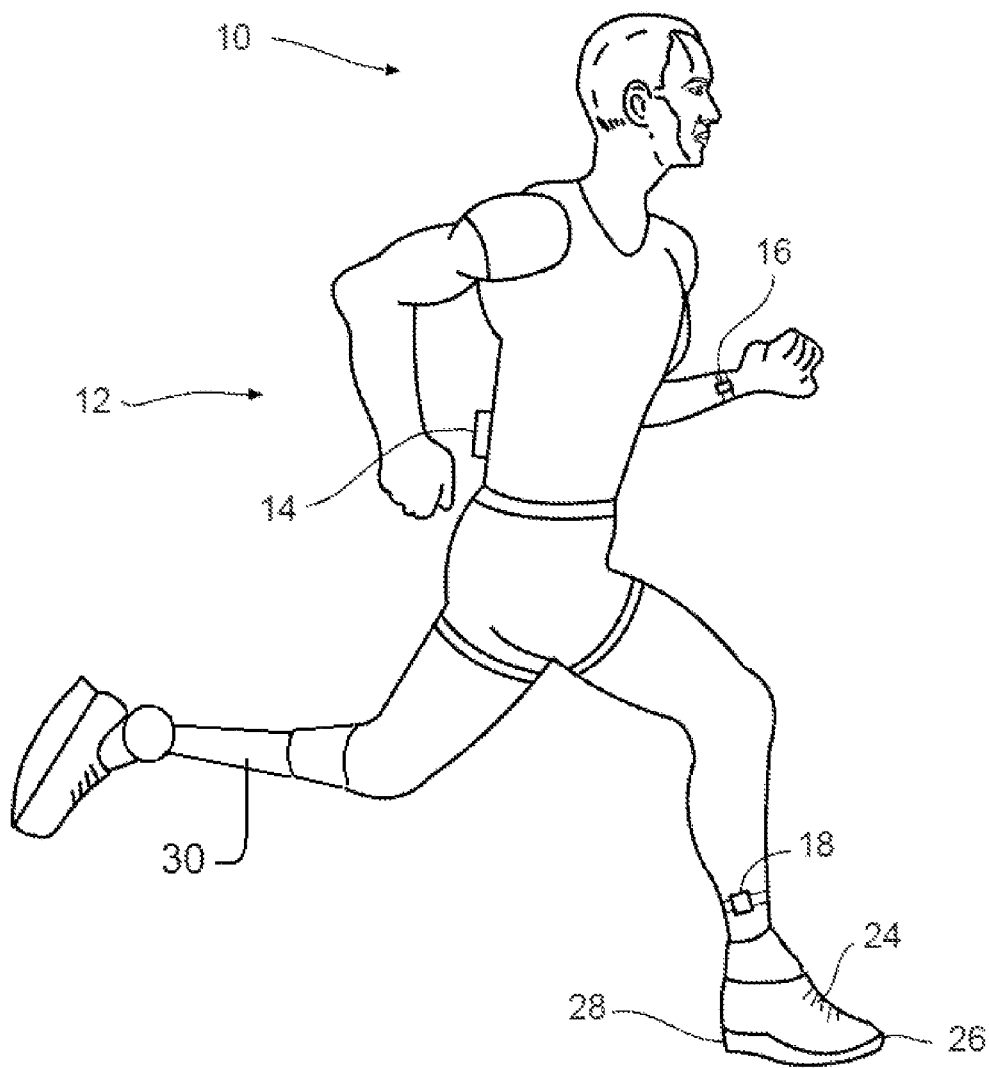
FIG. 2 is a schematic view similar to that of FIG. 1, showing a prosthetic leg.

As shown in FIG. 2, the runner has a prosthetic leg 30. The monitoring process for the human body activity can include measuring the motion of a movable prosthetic or human body part having an associated orthotic using one or more measurement devices applied to the movable prosthetic or to the human body part having an associated orthotic during activity of the human body, and calculating a movement economy profile of the human body movement using the data from the measurement devices, where the movement economy includes determining movement relative to speed of the human body, and modifying the prosthetic or orthotic in response to the movement economy profile.

The modification of the prosthetic or orthotic can occur in a number of ways. The position of the prosthetic or orthotic with respect to the human body can be modified. The shape of the prosthetic or orthotic can be adjusted, and the weight of the prosthetic or orthotic can be adjusted. A comparison of the control entropy with a database containing data pertaining to control entropy information of other subjects can be made, and a modification of the prosthetic or orthotic can be based on the comparison of the measured data with the data from the database. Further, one or more of the measurement devices can be applied to a human body part not having an associated orthotic in addition to the measurement devices applied to the prosthetic or human body part having the associated orthotic. Also, the motion of the movable prosthetic or human body part having an associated orthotic can be monitored repeatedly or periodically, and an assessment can be made as to whether the motion of the movable prosthetic or human body part having an associated orthotic changes from an initial motion. In addition, the modification of the prosthetic or orthotic can include adjusting the prosthetic or orthotic with respect to the human body to achieve a higher control entropy. Further, the modification can include adjusting the prosthetic or orthotic body part with respect to the human body to achieve a higher control entropy.

The monitoring process for human body activity can include measuring the motion of a movable prosthetic or human body part having an associated orthotic using one or more measurement devices applied to the movable prosthetic or human body part having an associated orthotic during activity of the human body, and calculating the control entropy of the movement of the prosthetic or human body part having an associated orthotic using the data from the measurement devices. Then, the prosthetic or orthotic can be modified in response to the control entropy calculation using any of the methods disclosed above.

In another embodiment, the control entropy can be calculated over a period of time, and a state of fatigue can be determined. The response to the determination of the state of fatigue can be a change in the body motion, or a cessation of the exercise activity. Further, these changes can be made merely in response to a change in the calculated control entropy.

According to one embodiment, the measuring of the motion of movable body parts includes measuring the foot of the human body. As shown in the drawing, an accelerometer is placed at the top or shoelaces area 24 of a shoe 26. An accelerometer is placed at the heel 28 of the shoe. A movement profile of the human body movement of the foot can be developed using the data from the measurement devices. This method would be useful in more accurately measuring such human body movement as pronation. Once the movement of the foot is diagnosed, changes in the running motion or in the physical structure of the shoe itself can be modified in response. The information from the accelerometers 24, 28 at the shoelace area and heel can be combined with the data from the shank accelerometer 18 for additional information describing the movement of the foot during exercise. In a specific embodiment, the measurement device includes an accelerometer and a gyroscope.

Additional EBSN sensors can be applied to the shank to determine factors such as the work to swing the shank, as well as impact dissipation between the shank and COM. This information could prove useful in predicting soft tissue injury from overuse or loading.

While this description illustrates the method of monitoring human activity during exercise, it is to be understood that the principles described here can be applied to activity of other subjects, such as, for example the training of race or show horses, and the building and operation of robots.

The principle and mode of operation of this invention have been described in its preferred embodiments. However, it should be noted that this invention may be practiced otherwise than as specifically illustrated and described without departing from its scope.

What is claimed is:

1. A method of monitoring human body movement of a human body having a center of mass, and a number of movable body parts that move relative to the center of mass during exercise, the method comprising: having an exerciser performing a movement wherein the center of mass is continuously moved laterally or horizontally in space relative to one of the ground and a component of an exercise machine, and wherein one or more movable body parts are in motion relative to the center of mass; measuring the speed of the center of mass of the human body moving through space relative to one of the ground and a component of an exercise machine; measuring the acceleration of the one or more movable body parts relative to the center of mass using one or more measurement devices applied to the one or more movable body parts during movement of a human body; and determining a movement economy profile of the human body movement using the data from the measurement devices, where the movement economy includes determining the ratio of the movement of the one or more body parts relative to the speed of the center of mass of the moving human body.

2. The method of claim 1 in which the measurement device is one or more of accelerometers, gyroscopes, and GPS.

3. The method of claim 1 including comparing the movement economy profile information with a database containing data pertaining to movement economy profile information of other subjects.

4. The method of claim 3 including modifying the movement of the human body in response to the movement economy profile information.

5. The method of claim 1 in which the measurement devices are accelerometers that are arranged to measure acceleration in three axes: anterior/posterior, vertical, and medial/lateral.

6. The method of claim 1 including treating the movement economy profile information according to one or more of the following: transmitting the movement economy profile information to a web-based device, storing the movement economy profile information in a data storage device, displaying the movement economy profile information, comparing the movement economy profile information with a database containing data pertaining to movement economy profile information of other subjects, and printing the movement economy profile information.

7. The method of claim 6 including modifying the movement of the human body in response to the movement economy profile information.

8. The method of claim 6 in which the measurement devices are accelerometers that are arranged to measure acceleration in three axes: anterior/posterior, vertical, and medial/lateral.

9. The method of claim 1 in which the gathering of the data from the accelerometers during movement of the human body occurs when the human body is moving in space and not on a stationary exercise machine.

10. A method of monitoring human body movement of a human body having a center of mass, and a number of movable body parts that move relative to the center of mass during exercise, the method comprising: having an exerciser perform a movement wherein the center of mass is continuously moved laterally or horizontally in space relative to one of the ground and a component of an exercise machine, and wherein one or more movable body parts are in motion relative to the center of mass determining the movement of the center of mass; measuring the motion of movable body parts relative to the motion of the center of mass of the body using one or more measurement devices applied to the one or more movable body parts during movement of a human body, where the one or more measurement devices are arranged to measure acceleration in three axes; and calculating the ratio of the measured motion of the one or more moveable body parts along of one of the axes to a resultant movement along all three of the axes.

11. The method of claim 10 in which the three axes represent the anterior/posterior, vertical, and medial/lateral directions.

12. The method of claim 10 including comparing the ratio with a database containing data pertaining to movement ratio information of other subjects.

13. The method of claim 10 including modifying the movement of the human body in response to the ratio information.

14. A method of monitoring human body movement of a human body having a center of mass, and a number of movable body parts that move relative to the center of mass during exercise, the method comprising: having an exerciser perform a movement wherein the center of mass is continuously moved laterally or horizontally in space relative to one of the ground and a component of an exercise machine, and wherein one or more movable body parts are in motion relative to the center of mass; determining the movement of the center of mass; measuring the motion of movable body parts relative to the motion of the center of mass of the body using one or more measurement devices applied to the movable body parts during movement of a human body; and determining a control entropy of the movement of the human body from the measured motion of the movable body parts.

15. The method of claim 14 including comparing the control entropy with a database containing control entropy information of other exercise subjects.

16. A method of claim 14 where the motion occurs over a period of time and the measurement is made at multiple times during the period of time, and further including calculating the control entropy of the movement of the human body over the period of time, and determining when a state of fatigue for the human body is reached based on the calculated control entropy.

17. The method of claim 16 including ceasing the human body movement when the control entropy changes.

18. The method of claim 14 including modifying the movement of the human body in response to the control entropy information.

19. The method of claim 14 including determining physical constraints on the human body during the human body movement using the control entropy information.

20. The method of claim 14 in which the measurement devices are accelerometers that are arranged to measure acceleration in three axes: anterior/posterior, vertical, and medial/lateral.

* * * * *